United States Patent
Reilly

(10) Patent No.: US 8,309,538 B2
(45) Date of Patent: Nov. 13, 2012

(54) CAPSAICINOID DECONTAMINATION COMPOSITIONS AND METHODS OF USE

(75) Inventor: Christopher A. Reilly, Salt Lake City, UT (US)

(73) Assignee: Kapso, LLC, Salt Lake City, UT (US)

( * ) Notice: Subject to any disclaimer, the term of this patent is extended or adjusted under 35 U.S.C. 154(b) by 292 days.

(21) Appl. No.: 12/634,418

(22) Filed: Dec. 9, 2009

(65) Prior Publication Data
US 2010/0086626 A1   Apr. 8, 2010

Related U.S. Application Data

(62) Division of application No. 11/366,327, filed on Mar. 2, 2006, now abandoned.

(60) Provisional application No. 60/658,822, filed on Mar. 4, 2005.

(51) Int. Cl.
*A01N 37/36* (2006.01)

(52) U.S. Cl. ......... 514/162; 514/823; 514/836; 514/975

(58) Field of Classification Search ................... 514/162
See application file for complete search history.

(56) References Cited

U.S. PATENT DOCUMENTS 6,071,541 A * 6/2000 Murad .......................... 424/616
2003/0031727 A1 * 2/2003 Hahn et al. .................... 424/617

OTHER PUBLICATIONS

Smith et al. "The Use of Chemical Incapacitant Sprays: A Review"; 2002; J. Trauma; 52:595-600.*

* cited by examiner

*Primary Examiner* — Timothy Thomas
(74) *Attorney, Agent, or Firm* — Maschoff Gilmore & Israelsen

(57) ABSTRACT

A method for cleansing and treating skin exposed to a capsaicin or derivative thereof so as to inhibit capsaicin reactivation includes: providing a subject having exposure to capsaicin, oleoresin capsicum, or other capsaicinoid derivative; cleansing capsaicin, oleoresin capsicum, or other capsaicinoid derivative from skin of the subject with a cleansing composition having: a carrier; a surfactant and/or detergent; a chelating agent; and salicylic acid, acetylsalicylic acid, or ibuprofen; and treating the skin of the subject with a therapeutic composition so as to inhibit reactivation of effects of capsaicin, oleoresin capsicum, or other capsaicinoid derivative exposure, the therapeutic composition having: a carrier; aloe; a thickening agent; and salicylic acid, acetylsalicylic acid, or ibuprofen.

4 Claims, 6 Drawing Sheets

Trace of Flare Reactions from Photomicrographs of Human Forearm Skin Treated with Capsaicin 1mg/mL in Ethanol

CAPSAICINOID DECONTAMINATION COMPOSITIONS AND METHODS OF USE

CROSS-REFERENCE TO RELATED APPLICATIONS

This utility application claims benefit of U.S. application Ser. No. 11/366,327, filed Mar. 2, 2006 and U.S. Provisional Application 60/658,822, filed Mar. 4, 2005, which applications are incorporated herein by reference in their entirety.

BACKGROUND OF THE INVENTION

1. The Field of the Invention

The present invention relates to compositions for decontaminating skin exposed to capsaicinoid and/or other chemical irritants. More particularly, the present invention relates to compositions for cleansing capsaicinoids from the skin, inactivating capsaicinoid receptors, and treating or otherwise mitigating the physiological responses associated with capsaicinoid exposure and receptor activation.

2. The Relevant Technology

Capsaicinoids are a group of pungent natural products that are isolated from the dried fruits of chili peppers (e.g., *Capsicum frutescens*) via extraction such as with an organic solvent. The crude extract of peppers is called Oleoresin *Capsicum* ("OC") and contains a diverse variety of chemicals including significant quantities of the capsaicinoids. There are six naturally occurring capsaicinoid analogues (shown in FIG. 1) that vary in concentration in peppers and OC: capsaicin (8-methyl-N-vanillyl-trans-6-nonenamide) (35-55%); dihydrocapsaicin (8-methyl-N-vanillylnonaneamide) (30-50%); nordihydrocapsaicin (5-10%); nonivamide (n-vanillynonanamide) (<5%), homocapsaicin (1-5%); i and homodihydrocapsaicin (1-5%).

Hotter peppers (e.g., jalapeños) typically rated with higher Scoville Heat Unit values ("SHU") contain higher concentrations of capsaicin and dihydrocapsaicin than sweeter peppers (e.g., bell peppers) that contain only small quantities of dihydrocapsaicin and the other minor and less potent capsaicinoid analogues. Nonivamide (i.e., PAVA, VP, and Capsaicin II) has traditionally been referred to as synthetic capsaicin because of its facile laboratory synthesis and frequency of use as a surrogate for OC or crystalline capsaicinoid mixtures, but it has also been shown to be a natural product. Other structural analogues of nonivamide may also be used as surrogates for OC and will typically consist of a shorter or longer alkyl chain variants (e.g., heptyl, octyl decyl, etc). Both the aromatic vanilloid ring (3-OH-4-MeO-benzylamide) portion and the aliphatic chain (between 8-12 carbon atoms) are required for optimum pharmacological activity (e.g., activation of TRPV1, pain, etc.).

For centuries humans have used hot peppers, extracts, and capsaicinoids for a variety of purposes including traditional homeopathic treatment of various malaises such as dental pain, neuropathic pain, arthritis, stomach discomfort, antimicrobial defense, algesia, and as an aphrodisiac. Currently, cayenne pepper products and topical creams containing capsaicinoids are sold over-the-counter ("OTC") as dietary supplements and treatments to aid in digestion, stimulate metabolism and weight loss, and to help alleviate acute and chronic pain associated with acute injury, chronic inflammation, and neurogenic pain (e.g., Capzcin HP, Zostrix, Axsain, etc.). It has been reported that as early as 1850 dentists used alcoholic pepper extracts as an oral analgesic.

OC and capsaicinoids have also gained popularity as the active components for the production of self-defense weaponry known as less-than-lethal pepper spray products used by law enforcement and postal service employees as well as civilians. The products are used by law enforcement agencies worldwide to assist in the apprehension of non-compliant suspects and in crowd control. Postal workers and the general public also carry these products to help protect themselves against aggressive attack by animals and other individuals. A recent variation of the traditional pepper spray is the use of friable projectiles, which are similar to paint balls and contain inert powder mixed with crystalline capsaicinoids as the crowd/suspect control agent. Some of the earliest documented uses of hot peppers and capsaicinoids as a means of self-defense date back to the Mayans who reportedly burned pepper plants to help ward off attacks.

Currently, a variety of pepper spray products are available to law enforcement personnel and the general public. These products vary in size, shape, labeling, etc. Regardless of these differences, many of these products are similar in their composition. The vast majority of pepper spray devices are prepared using OC, which is the concentrated oil obtained from extraction of hot peppers. This is a crude extract from peppers, containing hundreds to thousands of different chemicals that vary in concentration from extract to extract, each possessing their own pharmacological and toxicological profiles. This extract is also the source for high concentrations of the capsaicinoids, the bioactive chemicals in pepper spray devices that are responsible for the irritant and pain producing properties characteristic of pepper spray products. Non-OC-based products typically consist of nonivamide (e.g., <2% w/v).

OC-based and non-OC-based pepper spray products are relatively simple. The solution for these products can be prepared by simple dilution of food-grade OC, approximately 5-100-fold (e.g., 1-20% v/v OC), using various solvents such as water, isopropyl or ethyl alcohol, other alcohols, propylene glycol, freons (e.g., CFC's), other organic solvents (e.g., TCE), or combinations of these substances. These dilute OC solutions are packaged in canisters and pressurized using a gaseous substance, such as air, nitrogen, carbon dioxide, propane, isobutane, combinations thereof, and the like. Some manufacturers have employed a highly volatile solvent system to prepare their products, and, thus, the solvent also serves as the propellant by maintaining pressure in the canister by solvent evaporation to form a gas. Typical OC-based pepper spray devices can be effectively dispensed between 5 to 20 times using sequential 1-second pulses from a range of 5-30 ft, depending upon the product and environmental conditions.

Pepper spray weapons are designed to deliver concentrated solutions of capsaicinoids to the eyes, skin and respiratory tract. When pepper sprays are used, the capsaicinoids present in the product activate TRPV1 (i.e., the capsaicin receptor, VR1) and possibly other sensory receptors and cause the characteristic physiological effects described below. The overall intended effects are temporary and safe incapacitation of the subject through pain, temporary blindness, disorientation, and compromised respiration.

There are many factors that can influence the performance and safety of pepper spray devices including the strength and characteristics of the capsaicinoid solution, as well as the efficiency and accuracy of delivery of the product. It has recently been shown that the vehicle composition of the product drastically influenced absorption of capsaicinoids into skin (i.e., stratum corneum) and into the dermis where sensory nerves dictate the pharmacodynamics of these products. Individual differences in sensitivity to the capsaicinoids, tolerance, case-specific differences (e.g., drug use, goal orientation, and altered mental status), and environmental conditions (e.g., space, ventilation, and wind) can also influence the performance and safety of these products. In general, however, the most important determinant of product efficacy and safety is the amount of capsaicinoids delivered to the targeted subject.

Recent research has demonstrated significant variability in the concentrations of capsaicinoids in OC-based pepper spray products. Representative manufactures of OC-based pepper spray products include First Defense, Defense Technologies, Guardian Personal Security Products, Inc., Security Plus, AERKO International, DMA, Mace Security International, Inc., Guardian Protective Devices, ChemArmor, Counter Assault Tactical Systems, UDAP Industries, and others. Analysis of multiple, randomly-selected commercial pepper spray products used by law enforcement personnel and the general public has demonstrated that the concentration of capsaicinoids in these products varied up to 100-fold. In addition, this variability was independent of the brand name, manufacturer, labeled SHU rating, and % OC listed on the canister. In other words, not all 10% OC products that were rated at 2 million SHU were equal in strength. In fact, one manufactured product that purportedly contained only 5% OC at 2 million SHU contained much higher concentrations of capsaicinoids than some of the 10% OC sprays also rated at 2 million SHU, and two manufactured 10% OC sprays were visibly much different in color and varied significantly in their concentrations of active ingredients despite the canisters having identical labels and origins. These studies demonstrated that the actual potency for many pepper spray products, as represented by labeled % OC and SHU value, was not representative of the true strength of the product. Such differences in the concentration of active ingredients may be a major contributing factor for the variability in performance and safety of these products.

Capsaicinoids selectively interact with TRPV1 (i.e., capsaicin receptor, VR1) or other sensory receptors to promote a complex array of physiological effects. Many of these effects are initiated through the initial stimulation of capsaicinoid receptors to promote massive increases in cytosolic calcium and sodium ions. This initial process initiates neuronal action potentials to produce the immediate sensation of pain and burning, elicits behavioral responses, as well as complex sequences of events within cells and the surrounding tissues including the release of substance P, CGRP, Neurokinin A and other pro-inflammatory substances and neuropeptides that mediate pain perception, irritation, and inflammation of the exposed sites. Although strategies to block the effects of substance P and NK1 receptors and the capsaicinoid receptors have been proposed as pain treatments, they are not practical due to limitations in drug delivery, stability, specificity, and availability. Additionally, an effective means of treating or preventing the physiological effects that arise from capsaicinoid exposure has not yet been provided. While the use of capsaicinoids has increased, there remains a need for a product to effectively cleanse and decontaminate sites of capsaicinoid exposure.

Therefore, it would be advantageous to have compositions capable of cleansing and/or decontaminating subjects that have been exposed to capsaicinoids through various commercial products. More particularly, it would be beneficial to be able to treat, mitigate, or prevent the undesirable physiological effects associated with capsaicinoid exposure.

SUMMARY OF THE INVENTION

Generally, the present invention relates to capsaicinoid cleansing compositions, capsaicinoid decontamination compositions, and/or therapeutic compositions that treat the physiological effects of capsaicinoids as well as the associated methods of cleansing and/or decontaminating capsaicinoid exposure and solution preparation. Also, the present invention relates to cleansing compositions, decontamination compositions, and/or therapeutic compositions that can cleanse, decontaminate, or treat exposure to other chemicals that are irritating to the skin.

In one embodiment, a cleansing composition can be configured to absorb or otherwise remove a capsaicin or other chemical irritant from skin exposed thereto. The cleansing composition can include the following: a carrier comprised of water and a thickening agent in an amount and form sufficient to be applied to the skin and contact cleansing agents thereto; a surfactant in an effective amount within the carrier sufficient to transport the capsaicinoid from the skin and into the carrier; a chelator in an effective amount within the carrier sufficient to chelate free calcium at the skin; and at least one of a keratinolytic agent or an antipyretic agent in an effective amount sufficient to provide keratinolytic activity or antipyretic activity.

In one embodiment, a therapeutic composition can be configured for treating, mitigating, and/or preventing physiological responses elicited by exposure to a capsaicinoid, chemical irritant, and/or environmental irritant. The therapeutic composition can include the following: a carrier comprised of water and a thickening agent, the carrier being present in an amount and form sufficient to be applied to skin and deliver active agents to the skin; a cooling agent in an effective amount within the carrier to provide a cooling sensation to the skin; a capsaicin receptor antagonist in an effective amount within the carrier to inhibit calcium flux associated with activation of the capsaicin receptor by a capsaicinoid; and, optionally, an anti-inflammatory agent in an effective amount within the carrier so as to be capable of penetrating into the skin and reducing inflammation associated with the exposure.

In one embodiment, a decontamination composition can be configured for cleansing and treating skin exposed to an irritant. The decontamination composition can include the following: a carrier comprised of water and a thickening agent, the carrier being present in an amount and form sufficient to be applied to the skin, absorb capsaicinoids from the skin, and deliver active agents to the skin; a surfactant in an effective amount within the carrier sufficient to transport the capsaicinoid from the skin and into the carrier; a chelating agent in an effective amount within the carrier sufficient to chelate free calcium at the skin; a cooling agent in an effective amount within the carrier to provide a cooling sensation to the skin; a capsaicin receptor antagonist in an effective amount within the carrier to inhibit calcium flux associated with activation of the capsaicin receptor by a capsaicinoid; and at least one of a keratinolytic agent, antipyretic agent, or anti-inflammatory agent in an effective amount sufficient to provide keratinolytic activity, antipyretic activity, or anti-inflammatory activity.

In one embodiment, the present invention can include a kit for cleansing and treating skin exposed to an irritant. Such a kit can include a cleansing composition and a therapeutic composition. The cleansing composition and/or the therapeutic composition can be in the form of a liquid, paste, gel, cream, and can optionally be impregnated within an absorbent matrix, such as a wipe, sponge, tissue, or the like. The cleansing composition can include a carrier, a surfactant, a chelating agent, and at least one of a keratinolytic agent, anti-inflammatory agent, or an antipyretic agent. The therapeutic composition can include a carrier, a cooling agent, and a capsaicin receptor antagonist.

In one embodiment, the present invention can include a method for cleansing and treating skin exposed to an irritant, such as a capsaicin or other chemical. The method can include applying a cleansing composition to the exposed skin in an amount sufficient to absorb the capsaicinoid into the cleansing composition, and applying the therapeutic composition to the cleansed skin in an amount sufficient to inhibit or treat physiological effects associated with exposure to the irritant. Optionally, the cleansing composition can be removed from the skin before applying the therapeutic composition.

These and other embodiments and features of the present invention will become more fully apparent from the following description, drawings, and/or appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only some embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

Figure 1:
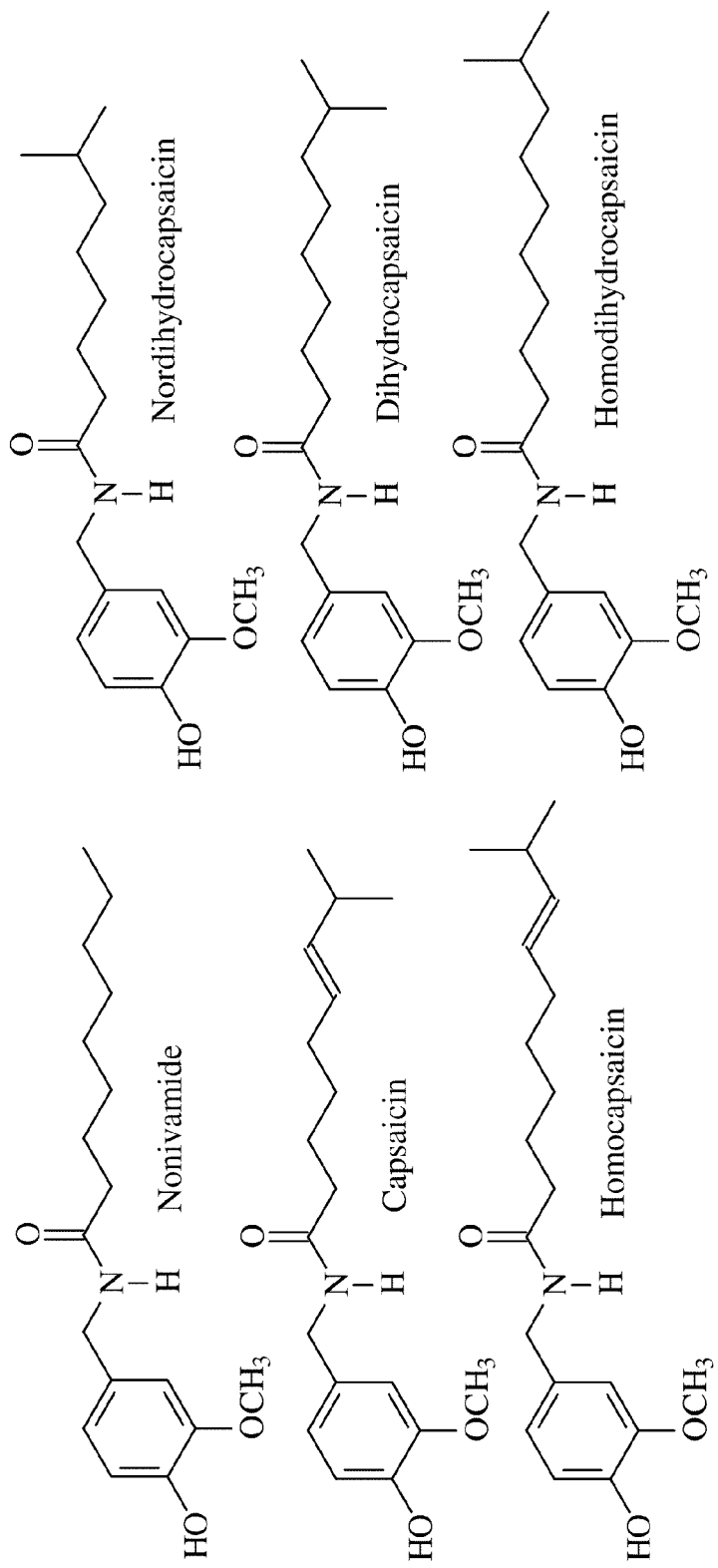
FIG. 1 provides diagrammatic illustrations of capsaicin analogs.

Generally, the present invention relates to capsaicinoid cleansing compositions, capsaicinoid decontamination compositions, and/or therapeutic compositions as well as the associated methods of cleansing and/or decontaminating capsaicinoid exposure. As such, the compositions described herein can inhibit or minimize the effects of exposure to capsaicinoids (e.g., pepper spray) by focusing on and interfering with the specific physiological sequences of events that occur in an exposed individual, as mediated by the interaction of capsaicinoid receptors with the capsaicinoids. Similarly, the compositions can cleanse or decontaminate skin that has been exposed to other capsaicin-containing products such as those used as topical creams, in pepper ball projectiles, and other similar capsaicinoid compositions that contact a subject's skin.

Additionally, the present invention relates to cleansing compositions, decontamination compositions, and/or therapeutic compositions for cleansing and treating exposure to harmful or noxious chemicals. The compositions can be used in methods of cleansing and/or decontaminating exposure to such chemicals.

In one embodiment, the cleansing, decontaminating, and/or therapeutic compositions along with the associated methods of use can also be beneficial in response to non-capsaicinoid contaminations that do not exert their effects through TRPV1 receptor-mediated mechanisms such as other riot control agents used separately or in combination with pepper sprays (e.g., CS, CN, allylsulfides, gingerols, and other, yet undescribed substances that may be used for self-defense or crowd control products). These other types of contaminations may also be cleansed, decontaminated, and/or treated by the compositions and methods of use described herein. For example, the cleansing, decontamination, and/or therapeutic compositions, with minor modifications to the base formulations presented herein, may be beneficial for use in treating the physiological effects that arise after tear gas or other chemical irritant exposure.

In another embodiment, the cleansing, decontaminating, and/or therapeutic compositions can prevent and/or treat inflammation. Accordingly, these compositions can be particularly useful in preventing and/or treating acute inflammation and discomfort associated with muscle injury or impact wounds that produce bruising. Also, the decontamination and combination treatment compositions can be useful in treating skin inflamed from sunburn.

While the present invention is described in connection with cleansing, decontaminating, and/or treating capsaicinoid contamination, it should be recognized that the compositions and methods can also be used for other harmful or noxious chemicals. Thus, the embodiments of the present invention described herein can be applied to such other harmful or noxious chemicals.

I. Compositions

The present invention includes various compositions that can be used alone or in combination to cleanse and/or treat exposure to capsaicin or other chemical irritants. The compositions can be configured for absorbing the chemical irritant from the skin so that the amount or concentration of irritant is reduced. Also, the compositions can be configured for delivering beneficial agents into the skin to ameliorate adverse physical responses to the chemical irritant. The beneficial agents can range from cooling agents, chelators, keratinolytics, anti-inflammatories and the like that can aid in providing relief to skin that has been exposed to the irritant.

A. Cleansing Composition

In one embodiment, the present invention includes a cleansing composition for cleansing skin exposed to an irritant such as a capsaicin or other chemical. Accordingly, an embodiment of a cleansing composition in accordance with the present invention can be capable of absorbing a capsaicinoid from the skin. As such, the cleansing composition can include the following components: a carrier; a surfactant; a chelating agent; and at least one of a keratinolytic agent, anti-inflammatory agent, or an antipyretic agent. The carrier can be comprised of water and/or other medium present in an amount and form sufficient to be applied to the skin and provide cleansing agents to the skin. The surfactant can be present in an amount within the carrier sufficient to transport the capsaicinoid from the skin and into the carrier. The chelator can be present in an amount within the carrier sufficient to reduce the bioavailability of calcium ions in the skin. Also, the at least one of a keratinolytic agent, anti-inflammatory agent, or an antipyretic agent can be present in the carrier in an effective amount sufficient to provide keratinolytic activity, anti-inflammatory activity, or antipyretic activity.

In one embodiment, the cleansing composition can be a formulation that is prepared as a viscous fluid resembling a concentrated liquid dish soap, laundry detergent, or shampoo. An example of such a cleansing composition can include about 74% purified water, about 20% sodium lauryl ether sulfate ("SLES"), about 5% ethylenediamine, ethylenediamine tetraacetic acid ("EDTA"), and about 1% salicylic acid, wherein relative concentrations are by weight of the total composition. The water-SLES combination can remove the lipophilic or hydrophobic capsaicinoids from the skin by minor de-lipidation of the stratum corneum and/or enhanced capsaicinoid partitioning out of the skin. Additionally, the EDTA can chelate free calcium at/or near the skin surface that may participate in TRPV1 activation and/or activation of downstream signaling events. Moreover, the salicylic acid can impart multi-functional characteristics such as keratinolytic activity, anti-inflammatory activity, or antipyretic activity. The anti-inflammatory activity by an anti-inflammatory agent can attenuate downstream pro-inflammatory events associated with TRPV1 (i.e., capsaicin receptor, VR1) or other sensory receptor activation in skin and nerve cells, including cyclooxygenase function, cyclooxygenase induction, inflammatory cytokine release (e.g., IL-6, IL-8, IL-1α,β, TNFα, Prostaglandins $D_2$, $E_2$, endogenous pyrogen, $F_{2\alpha}$, Leukotriene $B_4$, Prostacyclin $I_2$, etc.), and other inflammatory processes.

B. Therapeutic Composition

In one embodiment, the therapeutic composition can be a formulation that is configured to introduce and deliver into the skin active agents or substances that are capable of interfering with or short-circuiting the capsaicin receptor-mediated process and cascading signaling events that produce acute and prolonged pain and inflammation. However, it should be recognized that complete prevention of pain perception may not occur since these processes are immediate and have already been initiated by the initial exposure to the capsaicinoid. As such, the therapeutic composition can be configured to minimize these physiological sensations faster than natural physiological mechanisms for clearance, which can last up to about 24 through 48 hours after exposure. Thus, the therapeutic composition can be used for removing and/or inactivating the toxicant, decreasing the magnitude of the pain sensation, providing general capsaicinoid decontamination, and/or treating or preventing physiological effects that arise from capsaicinoid exposure.

In one embodiment, the therapeutic composition can include a gelatinized carrier, which can resemble an aloe gel, which contains capsaicin receptor inhibitors and other agents that have been shown to mitigate the effects of capsaicinoid receptor activation by exposure. The gel carrier can be retained on the skin for a sufficient duration to allow the active components to absorb into the skin while leaving behind a persistent aqueous-like barrier or layer that provides a cooling/soothing sensation to the skin surface.

Accordingly, an embodiment of a therapeutic composition in accordance with the present invention is capable of administering active agents into the contaminated skin. As such, the therapeutic composition can include the following components: a carrier, a thickening agent, a cooling agent, a capsaicin receptor antagonist, and an anti-inflammatory agent. The carrier can be present in an amount and form sufficient to be applied to the contaminated skin and deliver active agents thereto, where the inclusion of a thickening agent can provide the gelatinous characteristics for enhanced adhesion to the skin. The cooling agent can be present in an amount within the carrier to provide a cooling or soothing sensation to the skin. The capsaicin receptor antagonist can be present in an effective amount within the carrier to inhibit calcium flux associated with activation of the capsaicin receptor by a capsaicinoid. Also, the anti-inflammatory agent can be present in an effective amount within the carrier so as to be capable of penetrating into the skin and reducing inflammation associated with the capsaicinoid exposure.

An example of the therapeutic composition can include about 89% distilled water, about 9% aloe vera gel, about 0.5% salicylic acid, about 0.5% triethanolamine (e.g., trolamine), about 0.4% Carbomer Ultrez®, about 0.3% magnesium aluminum silicate (e.g., veegum), about 0.1% preservative (e.g., phenoxyethanol, methyparaban, ethyparaban, propylparaban), about 0.1% Mg-gluconate, about 0.1% Zn-gluconate, where relative concentrations are by weight of the total composition. The water and aloe vera gel provide a carrier for the active agents as well as a medium for adhering to the contaminated skin. Also, the aloe vera component is an active agent that exhibits a cooling effect when applied to the skin. Also, the salicylic acid is an active agent that can impart the multi-functional characteristics such as keratinolytic activity, anti-inflammatory activity, or antipyretic activity. Additionally, the trolamine can act as a buffer to neutralize the pH of the therapeutic composition and skin or tissue, as well as a permeation enhancer for increasing the rate of transdermal delivery of the active agents. The Carbomer Ultrez® is one example of a thickener or rheological agent that can act as a carrier and impart lotion, paste, cream or gel characteristics to the composition. The magnesium aluminum silicate is used as an emulsifier, suspending agent, and thickener, and results in thixotropy. The preservative is provided to impart antimicrobial characteristics. The Mg-gluconate and Zn-gluconate are active agents providing magnesium and zinc sources that can act as capsaicin receptor antagonists by competing with calcium so as to inhibit the amount of calcium flux associated with activation of the capsaicin receptor.

Additionally, the therapeutic composition can be modified to include various other components, such as an aloe vera gel base containing aspirin (i.e., acetylsalicylic acid; an anti-inflammatory agent shown to reduce the flare associated with dermal exposure to capsaicinoids), trolamine salicylate (i.e., an over-the-counter product used for inflammation and pain relief), and liquid antacid magnesium aluminum hydroxide, which is another substance shown to decrease the effects of capsaicinoids in skin. The mechanisms by which these substances promote relief involve the inhibition of cyclooxygenase-dependent inflammatory responses by salicylates, increasing and buffering the pH of the skin by the trolamine and metal hydroxides, and the competitive inhibition of the capsaicin receptor activity by magnesium, aluminum, and zinc ions. In part, buffering agents can be beneficial by counteracting adverse consequences of inflammation, which can produce a decrease in pH that exacerbates capsaicin receptor activation.

C. Decontamination Composition

In one embodiment, the present invention can include a decontamination composition for cleansing and treating skin that has been exposed to a capsaicinoid. Such a decontamination composition can be essentially a combination of the cleansing and therapeutic compositions and can include a carrier comprised of water and a thickening agent in an amount and form sufficient to be applied to the skin, absorb capsaicinoids from the skin, and deliver active agents to the skin. Additionally, a surfactant can be included in an amount within the carrier sufficient to transport the capsaicinoid from the skin and into the carrier. Also, a chelating agent can be included in an amount within the carrier sufficient to reduce the bioavailability of calcium ions in skin. Further, a cooling agent can be included in an amount within the carrier to provide a cooling sensation to the skin. Furthermore, a capsaicin receptor antagonist can be included in an effective amount within the carrier to inhibit calcium flux associated with activation of the capsaicin receptor by a capsaicinoid. The composition can also include at least one of a keratinolytic agent or an antipyretic agent in an effective amount sufficient to provide keratinolytic activity or antipyretic activity. Moreover, the decontamination composition can include at least one of the keratinolytic agent, anti-inflammatory agent, or an antipyretic agent being present in the carrier in an effective amount sufficient to provide keratinolytic activity, anti-inflammatory activity, or antipyretic activity. When used, the anti-inflammatory agent can be present in an effective amount within the carrier so as to be capable of penetrating into the skin and reducing inflammation associated with the capsaicinoid exposure.

D. Compositional Components

In accordance with any of the compositions described herein, the carrier can be comprised of water and additional components such as a thickener, rheological agent, or other medium that is routinely used for personal care and/or cosmetic products. The thickener or rheological agent can also be considered as a viscosity increaser because the viscosity of the composition can be changed with the addition of the thickener, which can result in the formation of a gel. Various polymers are representative of the viscosity increaser. Such polymers include carboxyvinyl polymers, polyhydroxyacids, alginates, polyacrylic acids, pentosans, polysulfates, polyorthoesters, polysaccharides, and the like. More particularly, thickening polysaccharides can include celluloses, amyloses, inulins, chitins, chitosans, amylopectins, glycogens, pectins, hemicelluloses, glucomannans, galactoglucomannans, xyloglucans, methylglucuronoxylans, arabinoxylans, methylglucuronoarabinoxylans, glycosaminoglycans, chondroitins, hyaluronic acids, alginic acids, and the like. Some more specific examples of thickening agents include carrageens, carboxymethylcellulose, hydroxyethyl cellulose, and water soluble salts of cellulose ethers such as sodium carboxymethylcellulose and sodium hydroxyethyl cellulose.

Also, natural gums such as gum karaya, xanthum gum, gum arabic, and gum tragacanth can be used as a thickening agent or rheological agent to further improve the texture to the composition. Some examples of thickening gum components can include sodium alginate, ammonium alginate, sodium calcium alginate, calcium alginate, potassium alginate, esters of alginic acid and the like. Thickening agents such as viscosity increasers can be used in an amount, for example, up to about 30% by weight of the composition, more preferably about 0.1% to about 20%, and most preferably about 0.2% to about 10%. However, the amount of thickener can vary depending on the other constituents in the composition.

Plasticizers can also be combined into the carrier to aid in providing an adequate gelatinous consistency, which may also affect the viscosity. Some examples of plasticizers include glyceryl triacetate, acetylated monoglyceride, glyceryl tributyrate, ethyl laurate, ethyl acetoacetate, diethyl tartrate, ethyl or butyl lactates, diethyl malate, ethyl oleate, castor oil, succinylated monoglycerides and the like. When used, the plasticizer can be included up to about 10% by weight, preferably from about 0.1% to about 8%, and most preferably from about 1% to about 5% by weight.

In accordance with embodiments of the present invention, the compositions can include surfactants. Suitable surfactants are reasonably stable and foam throughout a wide pH range. The surfactant may be anionic, amphoteric, zwitterionic, cationic, or mixtures thereof. For example, anionic surfactants can include the water soluble salts of alkyl sulfates having from about 8 to about 20 carbon atoms in the alkyl chain (e.g., sodium alkyl sulfate), and the water soluble salts of monoglycerides or sulfonates of fatty acids having from about 8 to about 20 carbon atoms such as sodium lauryl sulfate or sodium lauryl ether sulfate. Nonionic surfactants can be broadly designed as uncharged surfactants having a hydrophilic portion and a hydrophobic portion. The amphoteric surfactants useful in the present invention can include derivatives of aliphatic secondary and tertiary amines in which the aliphatic hydrocarbon chain can be straight chain or branched, and wherein one of the aliphatic chains contains from about 8 to about 18 carbon atoms. Also, the amphoteric surfactant can include an anionic water-solubilizing group such as, for example, carboxylates, sulfonates, sulfates, phosphates, and phosphonates. In any event, the surfactant can be formulated as a detergent for efficient removal of capsaicinoids from the skin. Specific examples of preferred surfactants include sodium lauryl ether sulfate, cocamidopropyl- or lauramidopropyl betains, and tweens (i.e., polyethylene glycol sorbitan esters). The surfactants can be included at from about 4% to about 60%, more preferably from about 8% to about 50%, and most preferably from about 10% to about 40% by weight of the composition.

In accordance with embodiments of the present invention, the compositions can include chelating agents. A chelating agent is a chemical used to bind metal ions to form a monodente or bi-dente ring structure with calcium. Chelating agents can stabilize or bind up a calcium ion so that it is unavailable for interacting with a capsaicin receptor or for calcium flux. Chelating agents prevent calcium from interacting with the capsaicin biological pathways by keeping calcium ions in a soluble form until removed. Some examples of chelating agents include EDTA, hydroxy-EDTA ("HEDTA"), nitriolotriacetic acid ("NTA"), citric acids, acetic acid, various amino acid and peptides, di- and tri-phosphates, pentasodium pentacetate, dipicolinic acid, and the like. The chelating agents can be present at a concentration range of about 0.1% to about 30%, more preferably about 0.5% to about 20%, and most preferably about 1% to about 10% by weight.

In accordance with embodiments of the present invention, the compositions can include cooling agents. Some examples of substances that can be considered physiological cooling agents include aloe vera, menthol, peppermint oil, acyclic tertiary and secondary carboxamides, 3-1-methoxy propan-1,2-diol, 2-isopropyl-N,2,3-trimethylbutyramide, N-ethyl-p-menthane-3-carboxamide, Menthone glycerol ketal, (−)-menthyl lactate, (−)-menthoxypropane-1,2-diol, (−)-isopulegol, cis & trans p-menthane-3,8-diols, (1R,3R,4S)-3-menthyl-3,6-dioxaheptanoate, (1R,2S,5R)-3-menthyl methoxyacetate, (1R,2S,5R)-3-menthyl 3,6,9-trioxadecanoate, (1R,2S,5R)-3-menthyl 3.6,9-trioxadecanoate, (1R,2S,5R)-3-menthyl (2-hydroxyethoxy)acetate & (1R,2S,5R)-menthyl 11-hydroxy-3,6,9-trioxaundecanoate, 1-[2-hydroxyphenyl]-4-[2-nitrophenyl-]-1,2,3,6-tetrahydropyrimidine-2-one), and the like. When used, cooling agents can be included at from about 0.001% to about 50% by weight of the composition, more preferably about 0.01% to about 35%, and most preferably about 0.1% to about 20% by weight.

The present invention may also include bicarbonate salts to buffer the pH of the compositions. Bicarbonate salts are soluble in water, and can release carbon dioxide into aqueous systems. Sodium bicarbonate is the preferred bicarbonate.

Additionally, the compositions may include other buffering agents such as, for example, hydroxides, carbonates, borates, silicates, phosphates, imidazoles, and mixtures thereof. Specific examples of buffering agents include monosodium phosphate, trisodium phosphate, sodium hydroxide, potassium hydroxide, carbonate salts, sodium carbonate, imidazole, pyrophosphate salts, citric acid, and sodium citrate. Buffering agents can be used in concentrations at from about 0.1% to about 20% by weight of the composition, more preferably about 0.5% to about 15%, and most preferably about 1% to about 10% by weight.

Also, the compositions can include an emulsifier such as glycerol monostearate, lecithin, fatty acid monoglycerides, diglycerides, propylene glycol monostearate and mixtures thereof. When used, the emulsifier can be present up to about 10%, and preferably from about 1% to about 8% by weight of the composition and most preferably about 2% to about 5% by weight.

In accordance with embodiments of the present invention, the compositions can include capsaicin receptor antagonists which interact with the receptor so as to inhibit calcium flux associated with activation of the receptor by a capsaicinoid. Generally, a capsaicin receptor antagonist is a divalent cation other than a calcium, which can be administered as a salt and dissociate into ion pairs. Accordingly, various divalent cations can be employed to block calcium from interacting with the capsaicinoid receptors. Some examples include Mg-gluconate, Zn-gluconate, and the like. Divalent salts can be present up to about 2% by weight, more preferably about 0.001% to about 1% by weight, and most preferably about 0.002% to about 0.5% by weight. On the other hand, higher concentrations could be used.

Further, any of the compositions in accordance with the present invention can include salicylic acid. Salicylic acid, or a salt or conjugate thereof, can be used to impart keratinolytic properties, antipyretic properties, and anti-inflammatory properties to any of the compositions. As such, the salicylic acid can be included in the cleansing composition so as to provide keratinolytic activity and aid in removing the outer surface of the skin so as to aid in also removing capsaicinoids therefrom. In any of the compositions, the salicylic acid can reduce fever and inflammation. The salicylic acid can be present from about 0.1% up to about 20% by weight, more preferably about 0.1% to about 10%, and most preferably about 0.1% to about 5% by weight.

Moreover, any of the compositions in accordance with the present invention can include an anti-inflammatory agent. The anti-inflammatory agent can be used to reduce the swelling and/or pain associated with capsaicinoid contamination. As such, a wide variety of anti-inflammatory agents can be used, which generally can be referred to as non-steroidal anti-inflammatory agents ("NSAID"), steroidal agents, and cyclooxygenase inhibitors. More particularly, the anti-inflammatory agent can be selected from the group comprising any well-known anti-inflammatory agent: such as acetaminophen, acetylsalicylic acid, ibuprofen, naproxen, and the like. However, any anti-inflammatory agent or pain reliever, such as those listed in the incorporated provisional application, can be used. The anti-inflammatory agent can be present at about 0.001% to about 10% by weight of the composition, more preferably about 0.1% to about 7.5% by weight, and most preferably about 0.1% to about 5% by weight.

In one embodiment, an antipyretic can be included. An antipyretic can act to prevent or reduce fever by lowering the body temperature from a raised state. As such, local delivery of an antipyretic can function locally, such as at a site contaminated with a capsaicin. Examples of an antipyretic agent can include acetylsalicylic acid and acetaminophen. Additionally, an antipyretic can be a febrifuges herbal supplement such as catnip, chamomile, sage, and yarrow. Also, selected alcohols, such as ethanol or isopropyl alcohol can function as local antipyretics via evaporation from skin.

Additionally, various other additives or active agents can be included in the compositions. Some examples include the following: (a) preservatives such as benzalkonium chloride, phenoxyethanol, methylparaban, ethylparaban, and propylparaban; (b) local anesthetics such as benzocaine (0-20%) or lidocaine (0-5%); (c) non-anabolic steroids such as hydrocortisone, progesterone, or dehydroepiandrosterone ("DHEA"); (d) alternate metal salts such as carbonates, phosphates, citrates, amino acid chelates, and the like; (e) Neurokinin Receptor inhibitors such as D-Arg1, D-Trp-7,9, Leu11SR48968, GR205171, L733060, sendide; (f) cannabinoid receptor agonists such as HU210, palmityletanolamide, 2-arachidonylglycerol, AM1241, and the like; (g) selective TRPV1 inhibitors such as capsazepine, SC0030, LJO-328, JYL series, PSY series, IBTU, BCTC, Iodo-RTX, halogenated capsaicinoids, capsaicinoid structural variants lacking agonist activity (e.g., n-benzylnonamide, 4-MeO-3-OH-nonivamide, 3-MeO-nonivamide, 3,4-DiMeO-nonivamide, etc.) and the like; (h) oxidants such as $H_2O_2$, benzoyl peroxide, organic hydroperoxides (e.g., cumene or tert-butyl hydroperoxide), and the like; (i) peptidases such as amidase, bromelain, and papain; (j) permeation enhancers for transdermal delivery of active agents, which include triethanolamine, DMSO, fatty acids, lecithins, metal hydroxides, glycerol monolaurate ("GML"), glycerol monooleate ("GMO"), and glycerol monolinoleate ("GMLO"), ethyl palmitate, and many others; (k) analgesics or other pain relievers, and (l) herbals such as peppermint (*Mentha piperita*), propolis (*Resina propoli*), arnica (*Arnica montana*; Leopard's Bain), German chamomile (*Chamomilla recutita*), oak bark, white willow bark (*salix alba*), ginger (*Zingiber officinale*), witch hazel (*Hamamelis virginiana*), winteracea (*Drymis winteri*), sangre de grado, and Korean ginseng, Chinese ginseng, Asian ginseng (*Panax Ginseng* Root), ginsenosides (*Panax quinquefolium*), where all herbs can be prepared as extracts and have some degree of anti-inflammatory potency via complex and largely undefined mechanisms, and some herbal agents have been shown to directly inhibit capsaicin responses. Also aminoglycoside antibiotics such as streptomycin, neomycin, gentamycin have been shown to inhibit TRPV1, and can also be useful as an anti-infective.

Additionally, the compositions can be modified to increase the efficacy and rate of relief by various compositional modifications to the exemplary formulations. Modifications to the cleansing composition can include detergents such as lauryl sulfate to facilitate capsaicinoid removal. Alternate surfactants such as tween may also be used, and removal of capsaicinoids from fabrics is greatly enhanced by lauryl sulfate. A second modification to cleansing compositions can include metal chelates with or in place of EDTA. The metal chelate can perform as an alternate mechanism of capsaicinoid receptor inhibition. Immediate treatment of the skin sites with competing metals may assist in short-circuiting the pain and inflammation processes at a very early stage. Also, the use of a hydrophobic metal chelate may potentially increase dermal uptake of the metal ions. Also, trolamine or a metal hydroxide such as NaOH can be used to neutralize the solution pH.

Modifications to the therapeutic composition can also involve a zinc compound or aluminum compound as an inhibitor of the capsaicin receptor. Also, the composition can be modified by any of the following: adding or increasing the amount of veegum; adding or increased MgOH; adding or increased AlOH; increased salicylic acid; adding or increasing acetylsalicylic acid to enhance the anti-inflammatory potential of the solution. Other modifications can include the addition of another cooling compound such as menthol, which has been recently shown to stimulate TRPM8 receptors that produce the sensation of cooling. Also, phenylephrine-HCl, a vasoconstricting agent that can assist with inflammation and erythemic responses by decreasing localized blood flow and plasma leakage as part of the inflammatory response, can be added to the therapeutic composition.

In addition to the aforementioned compositions and components, a wide array of components can be combined into a cleansing composition, inhibitory composition, and a decontamination composition. All of these components or substances have either direct effects on capsaicin effects or should theoretically disrupt processes that are involved in responses to capsaicin.

Furthermore, specific and potent antagonists or inhibitors of the capsaicin receptor have been developed and characterized. These are typically very effective in preventing ion flux and pain associated with vanilloid exposure. Similarly, high affinity ultra-potent agonists are being developed as counter-irritant analgesics, which can modulate TRPV1 expression and minimize sensory perception of capsaicinoids. Many of these substances are being developed as potential analgesics to treat chronic pain by independent researchers and pharmaceutical companies. As such, these receptor antagonists or inhibitors can be used and/or mixed into the foregoing compositions to impede the biological pathway so as to reduce inflammation or pain associated with capsaicinoid exposure.

In addition to the various formulations of the cleansing, decontaminating, and/or therapeutic compositions, these compositions can be used in methods for cleaning, decontaminating, and treating skin that has been exposed to capsaicinoids, as well as treat or prevent the physiological effects of such an exposure. As such, the different methods of using the foregoing compositions will be described in greater detail below.

II. Methods of Cleansing and/or Treating Skin Contamination

Heretofore, the adverse effects of skin contamination by exposure to capsaicinoids begin to subside, but do not go away, within 1-2 hours with varying degrees of side effects depending upon the individual and exposure scenarios. As such, use of the cleansing, decontamination, and/or therapeutic compositions described herein can be used to reduce the duration of such adverse effects or even inhibit the onset of such adverse effects. Thus, the use of these compositions can treat or prevent persistent minor coughing, airway irritation, congestion, enhanced thermal sensitivity, and/or hyperalgesia at exposed skin sites, ocular discomfort, continued accidental re-exposure, and re-activation of the painful sensations by heat.

Figure 2:
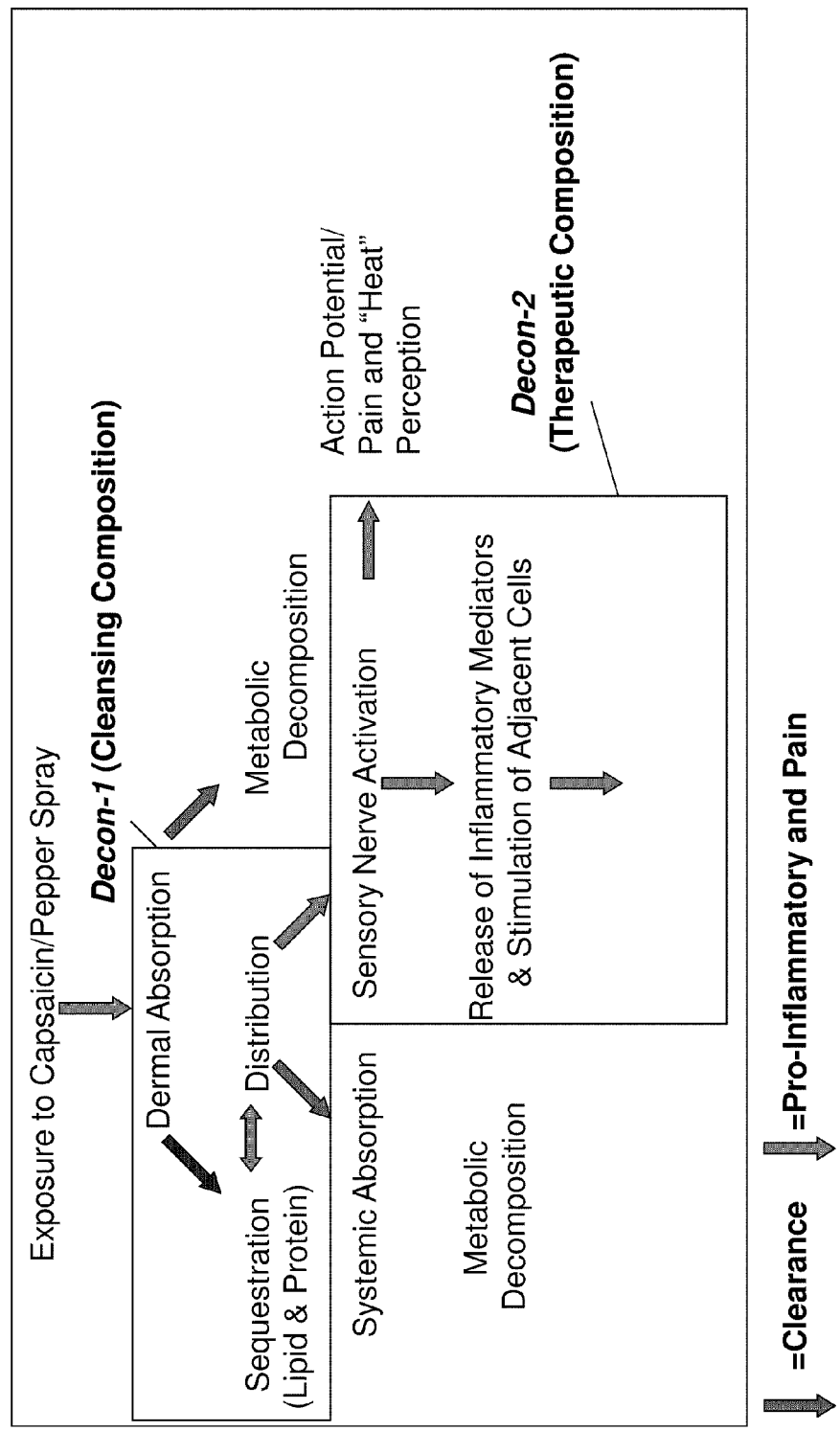
FIG. 2 is a schematic representation of a physiological response to capsaicin.

FIG. 2 illustrates a simulated capsaicin exposure. Accordingly, when skin is exposed to capsaicin, the capsaicin can absorb through the dermis. Such dermal absorption can result in the capsaicin being sequestered in lipids and proteins. The capsaicin can then diffuse from the lipids and proteins in order to produce adverse physiological actions well known to be associated with capsaicin exposure. Additionally, a portion of the absorbed capsaicin can be metabolized. During the absorption phase, it can be advantageous to apply a cleansing composition or decontamination composition to the skin. This can allow for the cleansing composition, exemplified by Decon-1, to absorb free capsaicinoids to inhibit further physiological activity. Also, such absorption can decrease the effective concentration of the capsaicin at the skin and increase diffusion of the sequestered capsaicin from the lipids and proteins.

After dermal absorption and sequestration, the capsaicin can then be distributed throughout the surrounding tissue and body. In one instance, the capsaicin is systemically absorbed where it can be metabolized. Alternatively, the capsaicin can be absorbed into tissues retaining sensory nerves, and can result in sensory nerve activation. The activation of the sensory nerves can then cause release of inflammatory mediators and thereby stimulate adjacent cells. This can lead to the person exposed to the capsaicin experiencing the action potential of pain and heat. During the activation phase, it can be advantageous to apply a therapeutic composition or decontamination composition to the skin. This can allow for the therapeutic composition, exemplified by Decon-2, to counteract the adverse effects of capsaicin and inhibit capsaicin receptor activation. Thus, the therapeutic composition can inhibit further physiological activity.

In one embodiment, the cleansing and/or decontamination compositions can be used to effectively remove as much capsaicinoid, pepper spray product, or irritating agent from the skin exposed thereto. As such, applying a cleansing composition to the contaminated skin can be referred to as the cleansing phase. In any event, the cleansing composition is applied to the skin in an amount that decreases the amount of capsaicinoid on the skin and/or in the skin. The cleansing phase can include a single or repeated (e.g., 2×, 3×, etc.) application of generous amounts of the cleansing composition to the skin. Blotting and/or wiping the skin clean so as to remove the cleansing composition and absorbed capsaicinoids from the skin can follow each application of the cleansing composition. Preferably, the cleansing composition is applied and removed by being impregnated within a wipe that can be wiped over the contaminated skin.

In one embodiment, the cleansing and decontamination of skin exposed to an irritant such as a capsaicinoid can be performed with the additional use of water. Such a method of cleansing and decontamination of skin can include the following: application of a sufficient amount of a cleansing composition to the skin; washing the skin vigorously immediately with the cleansing composition to produce a lather; rinsing with cold water to remove the lather; repeating the application, washing, and rinsing steps from 3 to 5 times within a few minutes; application of a sufficient amount of a therapeutic composition to the cleansed skin; reapplication of a sufficient amount of a therapeutic composition after the first application becomes dry on the skin; and reapplication as needed if discomfort persists.

In one embodiment, the cleansing and decontamination of skin exposed to an irritant such as a capsaicinoid can be performed without water. Such a method of cleansing and decontamination of skin can include the following: apply a sufficient amount of a cleansing composition to the skin; washing the skin vigorously immediately with the cleansing composition to produce a lather; wipe the lather from the skin with a cloth, towel, or the like; repeat the application, wash, and wipe steps, such as from 3 to 5 times within a few minutes; apply a sufficient amount of a therapeutic composition to the cleansed skin; reapply a sufficient amount of a therapeutic composition after the first application becomes dry on the skin; and reapply as needed if discomfort persists.

In one embodiment, the therapeutic compositions and/or decontamination compositions can be used to effectively inhibit a physiological response from skin exposure to a capsaicinoid, pepper spray product, or other irritating agent. Preferably, the therapeutic composition is applied to skin that has been cleansed, especially when cleansed by a cleansing composition in accordance with the present invention. As such, applying a therapeutic composition to the cleansed skin can be referred to as the treating or decontaminating phase. In any event, the therapeutic composition can be applied to the skin in an amount that inhibits the physiological repose to the capsaicinoid and sooths the skin. The treating or decontamination phase can include a single or repeated (e.g., 2×, 3×, etc.) application of generous amounts of the therapeutic composition to the skin. The therapeutic composition can then be left on the skin for an extended duration and reapplied as needed.

In one embodiment, the cleansing, decontamination, and/or therapeutic compositions can be used to decontaminate exposure to capsaicinoids. More particularly, the compositions can be used to treat or prevent a variety of physiological effects resulting from exposure to capsaicinoids such as severe dermal irritation that is characterized by an intense burning and itching sensation, erythema, reddening of the skin, and localized tissue inflammation due to plasma extravasations. Also, decontamination and treatment of the skin will tend to mitigate the uncontrollable coughing, shortness of breath, disorientation, confusion, and temporary blindness associated with exposure to capsaicin. Moreover, the compositions can treat or prevent other major symptoms of capsaicinoid exposure including uncontrollable coughing (capsaicin is a prototypical inducer of the cough reflex), shortness of breath, disorientation, confusion, and temporary blindness.

Additionally, use of the cleansing, therapeutic, decontamination, and/or therapeutic compositions can inhibit or prevent reactivation of capsaicinoid effects, which can result from exercise and/or exposure to elevated temperatures for up to 48 hours. Also, the compositions can inhibit or prevent capsaicinoid re-exposure, which can occur as long as capsaicinoids are present on the skin or proximate thereto. Also, use of these compositions can reduce loss of productivity and inhibit or prevent life-threatening and lethal consequences that result from short or prolonged exposures to capsaicinoids. As such, the compositions can minimize the drug-induced hyper-excitation and psychosis, as commonly observed in users of amphetamines, cocaine, alcohol, and other stimulants, which can result from capsaicinoid or other chemical irritant exposure.

In one embodiment, use of the cleansing, decontamination, and/or therapeutic compositions can inhibit the biological pathways associated with capsaicinoid contamination. As such, the biological pathways associated with the pharmacological properties of capsaicinoids can be inhibited or blocked so as to decrease the ability of capsaicinoids to interact with and stimulate the capsaicin receptors, and/or signaling pathways associated with capcaicinoid interactions. This can decrease the biological response associated with capsaicin receptors expressed by afferent peripheral sensory neurons (Aδ- and C-fibers) and other surrounding tissue and cell types (e.g., vascular, respiratory, and dermal epithelial cells). Briefly, the capsaicin receptor can activate a polymodal transmembrane cation channel that responds to various chemicals and environmental stimuli such as capsaicin, noxious temperature (e.g., >43° C.), and acidic pH (e.g., <6.3). In fact, the brain cannot distinguish between high temperatures, acid, and capsaicin without other sensory inputs (e.g., visual observations, etc.). Thus, these compositions can block or inhibit the physiological responses associated with such sensory inputs. Moreover, these compositions, especially the decontamination and treatment compositions, may be used to treat the redness, swelling, irritation, and pain associated with mild to acute sunburn.

Additionally, the cleansing, decontamination, and/or therapeutic compositions can reduce the ability of either temperature or pH changes to potentiate the receptor responses to capsaicinoids or from other receptor agonists such as resiniferatoxin, anandamide, and phorbol esters, thereby inhibiting or preventing such elevated responses. As such, these compositions can prevent or treat the physiological responses to any priming of TRPV1, VR1 or other associated receptors by a number of substances including histamine, leukotrienes, prostaglandins, other eicosanoids (e.g., HETEs, HPETEs), or changes in pH and temperature that may occur as a result of tissue injury and inflammation and contribute to capsaicinoid responses.

In one embodiment, use of the cleansing, decontamination, and/or therapeutic compositions can inhibit or block the physiological responses that result from activation of TRPV1, VR1, or capsaicin receptors, thereby inhibiting, reducing, or blocking increases of intracellular cytosolic calcium and sodium ions originating from extracellular and intracellular stores. Additional physiological responses that can be inhibited, reduced, or blocked include the concomitant depolarization of neurons that generate an action potential, as well as the concomitant degranulation that results in the release of substance P, CGRP, Neurokinin A and other chemokines and tachykinins that are involved in the pain perception and inflammation pathways. Thus, inhibiting, reducing, or blocking the release of these factors can prevent or treat the localized tissue inflammation (e.g., plasma leakage, CGRP effect, etc.), immune responses (e.g., inflammatory responses involving mast cell degranulation to initiate histamine responses and immune cell infiltration, including macrophages and lymphocytes; Substance P and NK effects), and painful burning and itching sensations.

In one embodiment, the cleansing, decontamination, and/or therapeutic compositions can inhibit, reduce, or block the complex array of physiological effects that arise from capsaicinoids selectively interacting with TRPV1, VR1, or other capsaicinoid receptors. As such, the inventive compositions can reduce the physiological effects that are initiated through the initial stimulation of capsaicinoid receptors so as to inhibit or reduce significant increases in cytosolic calcium and sodium ions. Thus, these compositions can inhibit, reduce, or block the subsequent complex sequence of events within cells and the surrounding tissues, which include the release of substance P, CGRP, Neurokinin A and other substances that mediate pain perception, irritation, and inflammation of the exposed sites.

In one embodiment, the cleansing, decontamination, and/or therapeutic compositions can inhibit, reduce, or block the foregoing negative physiological responses associated with capsaicinoid exposure by removing biologically active toxicants (i.e., capsaicinoids) from exposed sites. Additionally, the inventive compositions can inhibit, reduce, or block various points within the biochemical cascade of events that promote the physiological effects associated with capsaicinoid exposure, which specifically includes the inhibition of capsaicin receptor-mediated pro-inflammatory processes.

The foregoing uses of the cleansing, decontaminating, and/or therapeutic compositions can include applying the compositions to the skin, and removing the composition after the desire effect has been obtained. More particularly, a method for cleansing, treating, and/or decontaminating skin that has been exposed to a capsaicinoid can include acts of: applying a cleansing composition to the skin in an amount sufficient to absorb the capsaicinoid into the cleansing composition; removing the cleansing composition from the skin; and applying a therapeutic composition to the skin in an amount sufficient to inhibit or treat a physiological effect associated with capsaicinoid exposure.

In one embodiment, the methods of using the compositions can include applying the decontamination composition to the contaminated skin, and then removing the decontamination composition. Additionally, this act can be repeated until the desired effect is achieved or until the capsaicinoids have been removed from the skin. Optionally, the therapeutic composition can be administered to the skin after the decontamination composition has been removed. Thus, the decontamination composition can be substituted for the cleansing and/or therapeutic composition.

An ideal use for the compositions described herein would be a product that will address the skin irritation due to exposure of law enforcement chemical agents such as OC. The primary benefit of the present invention will be to reduce skin irritation faster than the traditional wash, air, and time. The present invention will also prevent reactivation of the capsaicin due to the presence of heat.

Also, for field application, the compositions can give immediate relief to the arrestee and or officer that have been hit with an OC pepper spray. The officers can use it to cleanse and decontaminate a subdued arrestee, and can cleanse and decontaminate themselves when they have been accidentally hit by a direct spray or blowback spray. Accordingly, the OC pepper spray cleansing and decontamination process may no longer be a huge problem for them, especially when they are accidentally contaminated. Moreover, the compositions can be beneficial from an officer-training standpoint where they are routinely hit with OC pepper spray in the training arena. Not only can the compositions treat skin OC contamination, but the compositions can also reduce the onset of eye irritation when removed from the surrounding skin. Even though the eyes do a good job of tearing and eventually cleaning out the eyes, the tearing function is too slow for an officer who is: (1) not intoxicated like most arrested subjects; (2) is not fighting and full of adrenaline like most arrested subjects; (3) not expecting a punishment as are most arrested suspects.

Additionally, the inventive compositions can be beneficial for officers who need to have the skin and eyes stop burning as immediately as possible so they can get back to training or work. Currently, officers in instructor schools that get a mere one-half second facial exposure are taking hours to days to fully recover. As such, full decontamination by use of the inventive compositions as quickly as possible is ideal. Additionally, the cleansing, therapeutic, and decontamination compositions can be packaged for easy use by officers or instructors.

In another embodiment, the decontamination or therapeutic compositions can minimize the effects of capsaicinoid exposure by being pre-applied before such exposure. In addition to reducing or inhibiting the immediate effects of capsaicinoid exposure, the previously treated skin can also be provided with attenuation of the long term effects of exposure. Also, pre-treated skin can be much more easily cleaned and decontaminated compared to untreated skin.

III. Delivery Platforms and Containers

The cleansing, decontamination and/or therapeutic compositions can be formulated into a delivery system and packaging for convenience and easy use. As such, the compositions can be prepared as liquids, gels, pastes, creams, and the like. Also, the compositions can be absorbed into absorbent matrices such as wipes, which can be used for the application of the compositions as described herein. The wipes impregnated with the compositions can be packaged into a unitary envelope having a separate side pouch for the cleansing composition and a separate side pouch for the therapeutic composition. This provides for one packaging system to include both of these compositions without cross-contamination.

Figure 3:
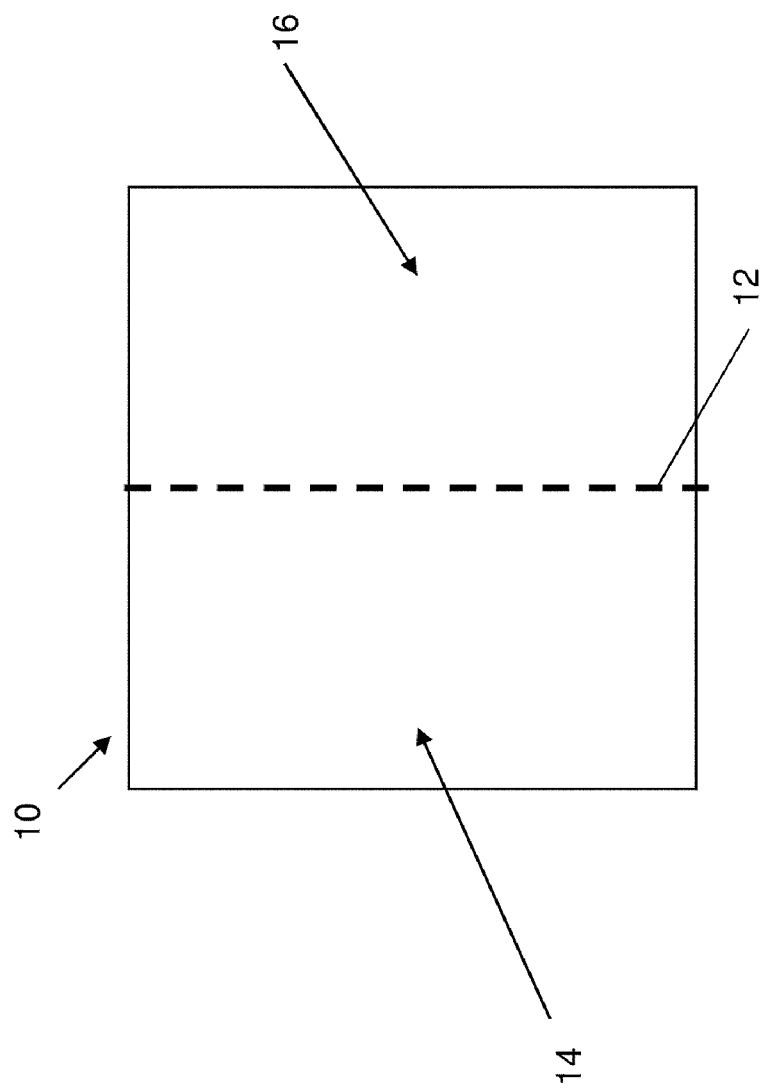
FIG. 3 is a schematic diagram of an embodiment of a multi-compartmental container in accordance with the present invention.

FIG. 3 illustrates an embodiment of a packaging system 10 including separate pouches as described above. Accordingly, the packaging system 10 can include a dividing seal 12 that separates a first compartment 14 from a second compartment. Optionally, each compartment 12, 14 can include one or a plurality of wipes impregnated with a composition in accordance with the present invention. Alternatively, each compartment can be filled with a gel, paste, cream or the like.

For example, each side pouch can have one or more 8½"× 12" towel or wipe. The cleansing composition can be impregnated into a wipe, and disposed in the cleansing pouch 14. Additionally, the therapeutic composition can be impregnated into a wipe, and disposed in the therapeutic pouch 16. Also, the two different towels and/or side pouches 14, 16 can be different colors from each other to aid in visual identification of the composition impregnated within the wipe. Moreover, the package system 10 can be about 9.5"×12.6" and is designed to be carried in the pocket, and each towel can folded over and is in a side pouch around 4½"×6". However, it should be recognized that these are merely representative sizes and configurations, and other embodiments may be used.

Alternatively, liquids, gels, pastes, creams, or wipes impregnated with cleansing composition, therapeutic composition, or decontamination composition can be supplied in rigid containers or soft packages. The containers can be easily carried and used in EMT, corrections and training. Each container or pouch can hold multiple towels and have easy access. Additionally, the different compositions can be included into a container such as a gel tub, pump spray container, and a stick-applicator container. In addition to the aforementioned types of containers, the compositions can be included in a pump sprayer. When the pump sprayer is used, it can be beneficial for the composition to be free-flowing so as to be capable of being sprayed onto the contaminated area. Also, the gel tub can be suitable container for gel, paste, or cream compositions that can be applied by hand or with a wipe. Moreover, the stick-applicator container can include any of the compositions formulated to be in the form of a stick or gel similar to a common deodorant or lip-balm container. As such, the various deodorant containers and composition configurations contained therein are representative of one embodiment of the present invention.

The following examples are provided to set forth to describe embodiments of the present invention. As such, these examples are not intended to be limiting but only examples of some of the embodiments of the present invention.

EXAMPLES OF EMBODIMENTS OF THE INVENTION

Example 1

Cleansing Composition

An embodiment of the cleansing composition was prepared in accordance with the principles of the present invention. The composition was formed by hydrating magnesium aluminum sulfate with water and mixing at high shear so as to homogenize the composition. The composition was then heated to about 80° C., and then xantham gum, EDTA, salicylic acid, and phenoxyethanol and parabens (butyl, ethyl, and methyl) were introduced into the high shear mixer. The mixing was slowed and zinc gluconate, magnesium gluconate, and sodium lauryl ether sulfate were then added. The composition was then cooled. The compositional concentrations are presented in Table 1:

TABLE 1

| |
|---|
| Water 73.85% |
| Sodium Laureth Sulfate 20% |
| Tetra Sodium EDTA 2% |
| Salicylic Acid 2% |
| Magnesium Aluminum Silicate 1.5% |
| Phenoxyethanol & Parabens (Butyl, Ethyl, Methyl, Propyl) 0.5% |
| Xanthan Gum 0.15% |
| Zinc Gluconate 0.001% |
| Magnesium Gluconate 0.001% |

Example 2

Therapeutic Composition

An embodiment of the therapeutic composition was prepared in accordance with the principles of the present invention. The mixing procedure was substantially the same as described in Example 1. Briefly, the composition was formed by hydrating magnesium aluminum sulfate with water and mixing at high shear so as to homogenize the composition. The composition was then heated to about 80° C., and then xantham gum, di-propylene glycol, EDTA, salicylic acid, and phenoxyethanol and parabens (butyl, ethyl, and methyl) were introduced into the high shear mixer. The mixing was slowed and zinc gluconate, magnesium gluconate, and aloe vera gel were then added. The composition was then cooled. The compositional concentrations are presented in Table 2:

TABLE 2

| |
|---|
| Water ~81.34% |
| Aloe Vera Gel 6% |
| Di-Propylene Glycol 5% |
| Magnesium Aluminum Silicate 3% |
| Salicylic Acid 2% |
| Tetra Sodium EDTA 2% |
| Phenoxyethanol & Parabens (Butyl, Ethyl, Methyl, Propyl) 0.5% |
| Xanthan Gum 0.15% |
| Zinc Gluconate ~0.001% |
| Magnesium Gluconate ~0.001% |

Example 3

Cleansing Capsaicinoid Exposure

Figure 4:
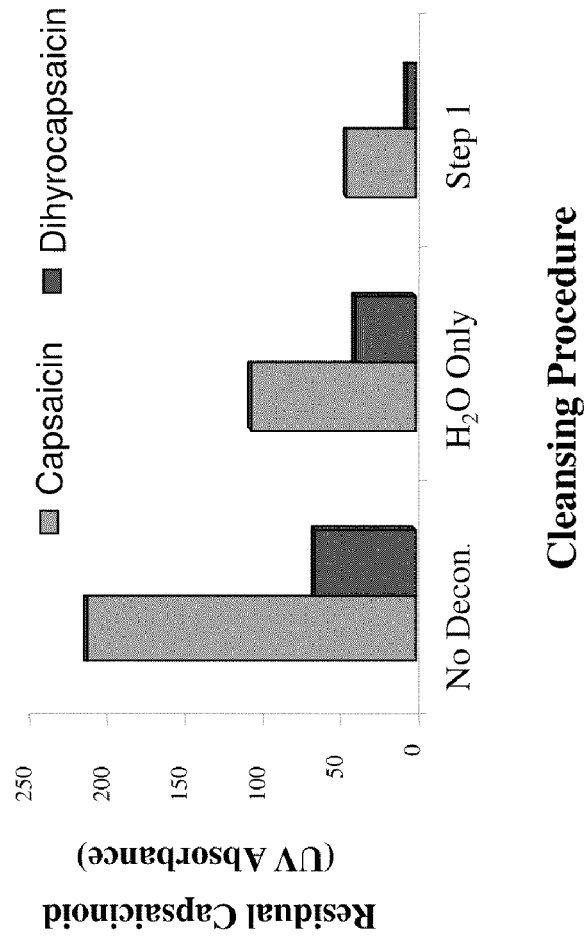
FIG. 4 is a graphical representation of a quantitative analysis of capsaicin analogs recovered from the treatment sites after treatment with embodiments of cleansing and therapeutic compositions and control cleansers.

The cleansing composition is prepared in accordance with Example 1 to test for cleansing efficacy. A subject was exposed to capsaicin extract (e.g., OC) by application to skin. The efficacy of the cleansing composition was compared with untreated skin and with a wash of only water. The capsaicinoid was removed from the subject's skin by applying the cleansing composition or water thereto followed by thorough removal. The application and removal of the cleansing composition and the wash with water only was performed three times. Neither the water only wash nor the cleansing composition had any benefit on the perception of pain, as expected. The amount of capsaicinoids (e.g., capsaicin and dihydrocapsaicin) remaining in the non-treated and washed skin was analyzed by HPLC. The results are shown in the graph of FIG. 4, which indicates that water alone can remove some capsaicinoids from the skin compared to the untreated control, and the cleansing composition effectively removes more capsaicinoids from the skin compared to water only wash.

Example 4

Cleansing and Decontaminating Capsaicinoid Exposure

The cleansing composition prepared in accordance with example 1 and the therapeutic composition prepared in accordance with Example 2 were tested for their cleansing and therapeutic efficacy. The combination of compositions was tested to determine the efficacy of mitigating the effects of capsaicinoid and pepper spray exposure after a subject was exposed to generous amounts of pepper spray product. The capsaicinoid was removed from the subject's skin by applying the cleansing composition thereto followed by thorough removal. The application and removal of the cleansing composition was performed three times. The cleansing composition had no benefit on the perception of pain, as expected; however, it was suspected that the capsaicin was adequately removed because the sites treated with therapeutic composition did not show any reactivation. Application of the therapeutic composition to the contaminated skin reportedly produced a moderate soothing sensation that effectively decreased the most severe effects of exposure to about 15 minutes. This time was much shorter compared to the typical 45 minutes to 2 hours duration of the negative and painful effects associated with an untreated exposure.

Additionally, the subject was exposed to hot water at the site of capsaicin contamination. Most notably, the reactivation of the capsaicinoid induced physiological effects upon subsequent exposure to hot water was greatly diminished by treatment with the cleansing composition followed by the therapeutic composition as compared to an untreated control. Reactivation of the capsaicinoid was observed on a portion of the skin that was not cleansed or treated. All treated sites were unresponsive to the hot water exposure and did not manifest any reactivation effects.

Example 5

Cleansing and Decontaminating Ethanolic Cayenne Exposure

The cleansing and therapeutic compositions prepared in accordance with Examples 1 and 2, respectively, were evaluated in their ability to decontaminate exposure to ethanolic cayenne extracts. A single drop of the ethanolic cayenne extracts were applied a subject's forearm skin at multiple demarcated sites and the alcohol was evaporated off, which allowed the capsaicinoids to penetrate the skin for about 5 minutes. The multiple test sites were not washed as a control, washed with water, or washed with two cleansing formulations. Following the wash steps, two therapeutic compositions were applied to the test sites. The sites were developed over a 10 minute period with a moist heat pad. The graphical results of exposure and treatment are shown in the FIG. 5.

Figure 5:
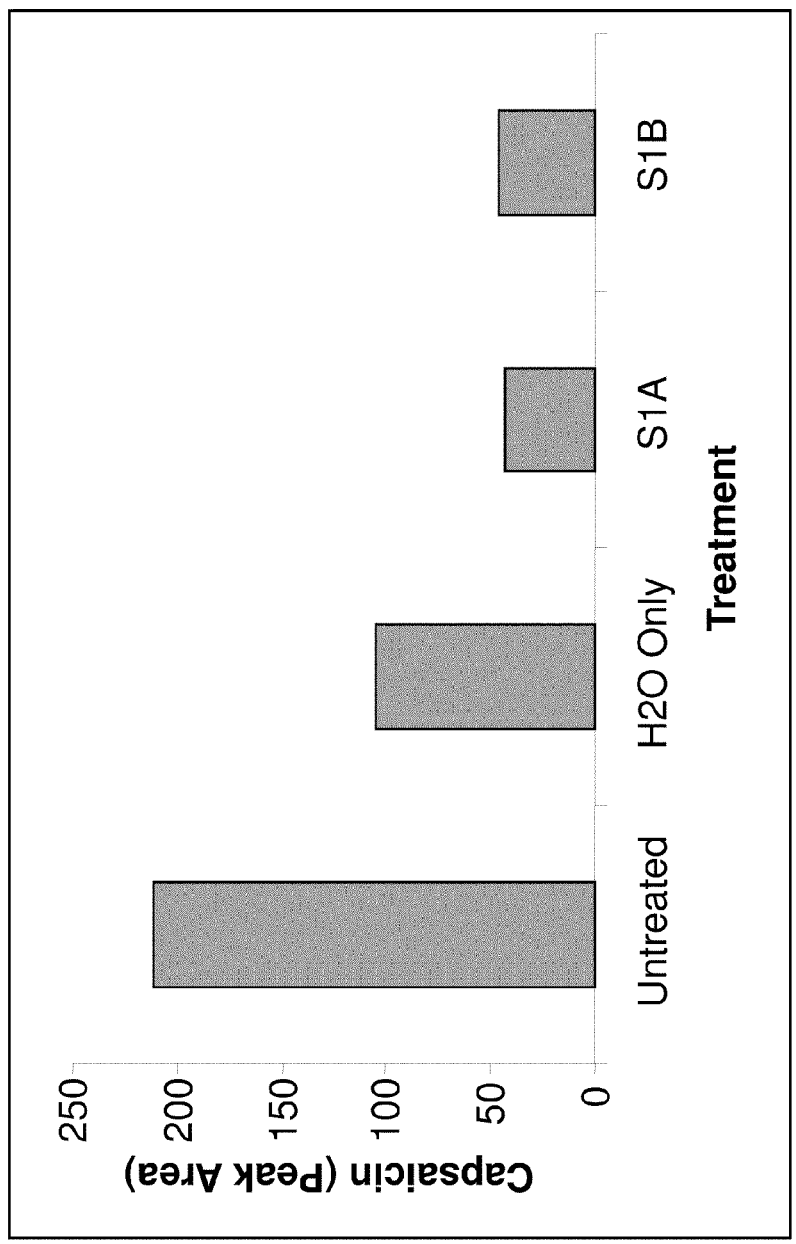
FIG. 5 is a graphical representation of an quantitative analysis of capsaicin analogs in skin following cleansing with an embodiment of a cleansing composition in accordance with the present invention.

Pain associated with exposure to heat after capsaicinoid cleansing and treatment was markedly lower in the treated sites relative to untreated and $H_2O$ site, which can be estimated on a scale of 10, with the treated sites being about a 2-3 compared to 10 at the untreated sites. Minimal redness was observed with washing with a cleansing composition (S1A or S1B) and treating with a therapeutic composition (S2A) site indicates significant decontamination of site as well as inhibition of the localized erythemic and inflammatory responses to capsaicinoids. Some mitigation of erythemic responses to capsaicinoids and heat was noticed with S1A and S1B use only, but pain was still detected. Additionally, FIG. 5 shows that washing with S1A or S1B cleansing compositions was more effective for removing capsaicinoids from the skin compared to washing with only water. Moreover, rubbing a therapeutic composition, such as S2A, onto the cleansed skin provided quick and lasting relief from pain and reactivation. Thus, the cleansing compositions can adequately remove the capsaicinoids from the skin, and addition of the therapeutic composition can significantly treat the physiological effects of capsaicinoid exposure.

Example 6

Cleansing and Decontaminating Ethanolic Cayenne Exposure

The cleansing and therapeutic compositions prepared in accordance with Examples 1 and 2, respectively, were evaluated in their ability to decontaminate exposure to ethanolic cayenne extracts and inhibit reactivation. A single drop of the ethanolic cayenne extracts were applied a subject's forearm skin at multiple demarcated sites and the alcohol was evaporated off, which allowed the capsaicinoids to penetrate the skin for about 5 minutes. The multiple test sites were not washed as a control, washed with water, washed with 70% isopropyl alcohol ("IPA"), washed with the cleansing composition alone, washed with the therapeutic composition alone, and washed with the cleansing composition followed by treatment with the therapeutic composition. The sites were developed over a 10 minute period with a moist heat pad. The results of reactivation of the skin of an arm after exposure and treatment are shown in the FIG. 6.

Figure 6:
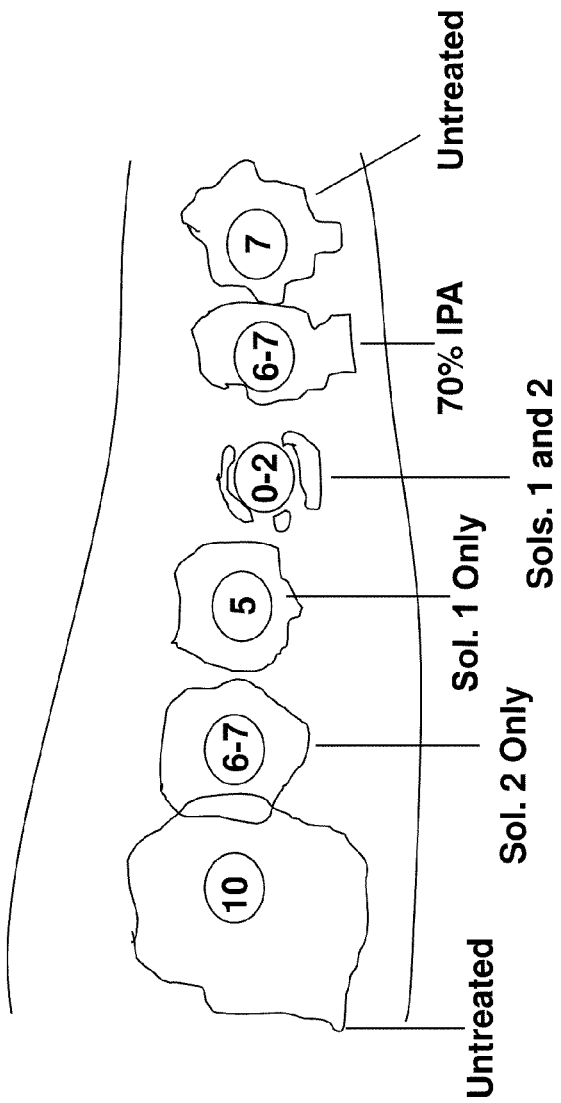
FIG. 6 is a schematic representation of reactivation skin irritation patterns from a comparative analysis of treatment with embodiments of cleansing and therapeutic compositions and control cleansers.

FIG. 6 shows a schematic representation of the results of the skin of an arm after exposure and treatment as described above following a reactivation with a moist heat pad. The circles are representations of the sites where the ethanolic capsaicin extracts were applied to the skin of the arm, and the larger "traces" represent the approximate outline of the flare of redness associated with the treatment and/or activation with the moist heat pad. As shown, the subjective flair and pain responses to a pin-scratch at the site after the various treatments are ranked from 10 being no response to 0 being completely cleansed and decontaminated.

In the graph of FIG. 4: "No Decon." indicates that no decontamination was conducted; "H$_2$O Only" indicates only water was used for decontamination; and "Step 1" indicates on the cleansing composition of "Step 1" was used for decontamination.

The untreated portion was determined to be reactivated by the moist heat pad to obtain from 7 to 10 on the pain scale. Cleansing with only IPA or the therapeutic composition resulted in reactivation by the moist heat pad to obtain from 6 to 7 on the pain scale. Cleansing with only the cleansing composition resulted in reactivation by the moist heat pad to obtain at about 5 on the pain scale. Cleansing with the cleansing composition followed by application of the therapeutic composition resulted in minimal to no reactivation by the moist heat pad so as to obtain from 0 to 2 on the pain scale. Thus, the combination of cleansing with the cleansing composition followed by treatment with the therapeutic composition can provide enhanced relief and inhibition of reactivation from exposure to a capsaicin.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for cleansing and treating skin exposed to a capsaicin or derivative thereof so as to inhibit capsaicin reactivation, method comprising:
   providing a subject having exposure to capsaicin, oleoresin capsicum, or other capsaicinoid derivative;
   cleansing capsaicin, oleoresin capsicum, or other capsaicinoid derivative from skin of the subject with a cleansing composition consisting of:
   water;
   sodium laureth sulfate and cocamidopropyl betaine;
   ethylenediamine tetraacetic acid (EDTA); and
   salicylic acid; and
   removing the cleansing composition and capsaicin from the skin prior to treating the skin with the therapeutic composition;
   treating the skin of the subject with a therapeutic composition so as to inhibit reactivation of effects of capsaicin, oleoresin capsicum, or other capsaicinoid derivative exposure, the therapeutic composition consisting of:
   water;
   aloe vera;
   magnesium aluminum silicate and xanthan gum; and
   salicylic acid.

2. A method for cleansing and treating skin exposed to a capsaicin or derivative thereof so as to inhibit capsaicin reactivation, method comprising:
   providing a subject having exposure to capsaicin, oleoresin capsicum, or other capsaicinoid derivative;
   cleansing capsaicin, oleoresin capsicum, or other capsaicinoid derivative from skin of the subject with a cleansing composition consisting of:
   water;
   sodium laureth sulfate;
   ethylenediamine tetraacetic acid (EDTA); and
   salicylic acid; and
   removing the cleansing composition and capsaicin from the skin prior to treating the skin with the therapeutic composition;
   treating the skin of the subject with a therapeutic composition so as to inhibit reactivation of effects of capsaicin, oleoresin capsicum, or other capsaicinoid derivative exposure, the therapeutic composition consisting of:
   water;
   aloe vera;
   magnesium aluminum silicate; and
   salicylic acid.

3. A method for cleansing and treating skin exposed to a capsaicin or derivative thereof so as to inhibit capsaicin reactivation, method comprising:
   providing a subject having exposure to capsaicin, oleoresin capsicum, or other capsaicinoid derivative;
   cleansing capsaicin, oleoresin capsicum, or other capsaicinoid derivative from skin of the subject with a cleansing composition consisting of:
   water;
   sodium laureth sulfate and cocamidopropyl betaine;
   phenoxyethanol, methylparaben, ethylparaben, butylparaben, and propylparaben;

ethylenediamine tetraacetic acid (EDTA); and
salicylic acid; and removing the cleansing composition and capsaicin from the skin prior to treating the skin with the therapeutic composition;

treating the skin of the subject with a therapeutic composition so as to inhibit reactivation of effects of capsaicin, oleoresin capsicum, or other capsaicinoid derivative exposure, the therapeutic composition consisting of:
water;
aloe vera;
phenoxyethanol, methylparaben, ethylparaben, butylparaben, and propylparaben;
magnesium aluminum silicate and xanthan gum; and
salicylic acid.

4. A method for cleansing and treating skin exposed to a capsaicin or derivative thereof so as to inhibit capsaicin reactivation, method comprising:

providing a subject having exposure to capsaicin, oleoresin capsicum, or other capsaicinoid derivative;

cleansing capsaicin, oleoresin capsicum, or other capsaicinoid derivative from skin of the subject with a cleansing composition consisting of:
water;
sodium laureth sulfate;
phenoxyethanol, methylparaben, ethylparaben, butylparaben, and propylparaben;
ethylenediamine tetraacetic acid (EDTA); and
salicylic acid; and removing the cleansing composition and capsaicin from the skin prior to treating the skin with the therapeutic composition;

treating the skin of the subject with a therapeutic composition so as to inhibit reactivation of effects of capsaicin, oleoresin capsicum, or other capsaicinoid derivative exposure, the therapeutic composition consisting of:
water;
aloe vera;
phenoxyethanol, methylparaben, ethylparaben, butylparaben, and propylparaben;
magnesium aluminum silicate; and
salicylic acid.

* * * * *